United States Patent
Semple et al.

(10) Patent No.: US 11,879,454 B2
(45) Date of Patent: Jan. 23, 2024

(54) METHOD AND APPARATUS FOR TESTING FOR AND REMOVING TRAPPED AIR FROM SUBMERSIBLE WELL PUMP ASSEMBLY

(71) Applicant: Baker Hughes Oilfield Operations LLC, Houston, TX (US)

(72) Inventors: Ryan Semple, Owasso, OK (US); Aron Meyer, Pryor, OK (US); Christopher Brunner, Owasso, OK (US)

(73) Assignee: BAKER HUGHES OILFIELD OPERATIONS, LLC, Houston, TX (US)

( * ) Notice: Subject to any disclaimer, the term of this patent is extended or adjusted under 35 U.S.C. 154(b) by 0 days.

(21) Appl. No.: 17/970,226

(22) Filed: Oct. 20, 2022

(65) Prior Publication Data

US 2023/0038803 A1    Feb. 9, 2023

Related U.S. Application Data

(63) Continuation of application No. 16/877,017, filed on May 18, 2020, now Pat. No. 11,525,442.

(51) Int. Cl.
| | |
|---|---|
| *F04B 53/06* | (2006.01) |
| *F04B 53/18* | (2006.01) |
| *G01N 33/28* | (2006.01) |

(52) U.S. Cl.
CPC .............. *F04B 53/06* (2013.01); *F04B 53/18* (2013.01); *G01N 33/2888* (2013.01)

(58) Field of Classification Search
CPC ...... F04B 53/06; F04B 53/18; G01N 33/2888
See application file for complete search history.

(56) References Cited

U.S. PATENT DOCUMENTS

| | | | |
|---|---|---|---|
| 5,169,522 A * | 12/1992 | Shalon | B01D 15/08 210/241 |
| 7,611,338 B2 | 11/2009 | Swatek et al. | |
| 8,419,390 B2 | 4/2013 | Merrill et al. | |
| 9,869,332 B2 | 1/2018 | Kennair, Jr. | |
| 10,125,759 B2 | 11/2018 | Pyron et al. | |
| 2011/0132687 A1 | 6/2011 | Ifield | |
| 2016/0169223 A1* | 6/2016 | Paul | F04B 9/12 417/63 |
| 2018/0017201 A1* | 1/2018 | Dupont | E21B 49/10 |

OTHER PUBLICATIONS

U.S. Non-Final Office Action dated Mar. 29, 2022, U.S. Appl. No. 16/877,017 (09010RF.045822).

* cited by examiner

*Primary Examiner* — Connor J Tremarche
(74) *Attorney, Agent, or Firm* — BRACEWELL LLP; Keith R. Derrington

(57) ABSTRACT

A fixture has a body that connects to a motor, the body having a bore. The body has a piston in the bore, separating the bore into a pressure chamber and a lubricant chamber in fluid communication with lubricant in the motor. A technician applies pressure to the pressure chamber, which causes the piston to increase pressure of the lubricant in the lubricant chamber and in the motor. The technician monitors a distance of movement of the piston, indicating a presence of residual air in the lubricant. If the movement meets a amount, the technician applies a vacuum to the lubricant chamber and bleeds out residual air from the lubricant in the motor.

8 Claims, 3 Drawing Sheets

METHOD AND APPARATUS FOR TESTING FOR AND REMOVING TRAPPED AIR FROM SUBMERSIBLE WELL PUMP ASSEMBLY

CROSS-REFERENCE TO RELATED APPLICATION

This application is a continuation of and claims priority to and the benefit of co-pending U.S. patent application Ser. No. 16/877,017 filed Mar. 5, 2020, the full disclosure of which is incorporated by reference herein in its entirety and for all purposes.

BACKGROUND OF THE INVENTION

1. Field of Invention

The present disclosure relates to electrical submersible well pump assemblies (ESP), and in particular to a method and apparatus for determining whether trapped air exists in dielectric lubricant in an ESP motor, and if sufficient, removing the trapped air.

BACKGROUND

Electrical submersible pumps (ESP) are commonly used in hydrocarbon producing wells. An ESP includes a pump driven by an electrical motor. The pump is often a centrifugal pump having impellers rotated by a shaft assembly extending from the motor. The motor is typically a three-phase AC motor.

A dielectric motor lubricant fills the motor to lubricate the bearings. A seal section mounts to end of the motor and has a shaft seal for sealing the motor lubricant from well fluid. A pressure equalizer has a movable element, such as an elastomeric bag or metal bellows, that has an interior in communication with the motor lubricant and an outer side that will be immersed in the well fluid. The pressure equalizer may be in the seal section or below the motor. The pressure equalizer reduces a pressure differential between lubricant in the motor and well fluid.

Motors may be filled with lubricant in a factory, at a field shop, or at the well site. One filling technique involves using a vacuum pump to withdraw air from the motor, then pumping the lubricant in from a lower end of the motor. Even with precautions, residual trapped air may be present when the ESP after filling. Trapped air can cause premature ESP failures due to over contraction of the pressure equalizer bag in the seal section. Over contraction may occur because of residual air pockets in the motor lubricant compressing during deployment and operation.

SUMMARY

A method of determining whether residual air is present within lubricant in an electrical submersible pump module and removing the residual air if a sufficient amount is found includes connecting a tubular body having a bore to an interior of the motor. The tubular body has a piston in the bore that defines a lubricant chamber in the bore that is in fluid communication with the lubricant in the motor.

The method further comprises applying a force on the piston, which causes the piston to increase pressure of the lubricant in the lubricant chamber and in the motor. A technician monitors a distance of movement of the piston, if any, in response to the fluid pressure being applied. If the distance meets a selected amount, indicating an unacceptable presence of residual air in the lubricant, the next step is removing the pressure in the lubricant chamber. Then the technician applies a vacuum to the lubricant chamber and bleeds out residual air from the lubricant in the motor.

In the embodiment shown, an indicator rod extends from the piston out an upper end of the body. Monitoring a distance of movement comprises noting the amount of protrusion of the indicator rod from the upper end of the body before the pressure is applied and after the pressure is applied.

Applying the vacuum comprises connecting a fluid line with a vacuum valve from the lubricant chamber to a bubble monitoring device. Also, a vacuum line will be connected from a vacuum pump to the bubble monitoring device. The next step is operating the vacuum pump to suction lubricant from the lubricant chamber through the fluid line to the bubble monitoring device. A technician controls the vacuum being applied to prevent lubricant from flowing past the bubble monitoring device to the vacuum pump but allowing air bubbles detected by the bubble monitoring device to flow to the vacuum pump.

In the embodiment shown, the bubble monitoring device is a sight glass. The vacuum line extends from the vacuum pump to an opposite end of the sight glass. The technician operates the vacuum pump to suction lubricant from the lubricant chamber through the fluid line and the vacuum valve into the sight glass while viewing the sight glass. The technician controls the vacuum valve to prevent lubricant that has moved into the sight glass from flowing to the vacuum pump but allowing air bubbles visible in the lubricant in the sight glass to flow to the vacuum pump.

In the embodiment shown, the piston has a port extending from its lubricant side to its pressure side. A fluid line extends from the port out the upper end of the body. Applying the vacuum comprises cooperatively connecting a vacuum pump to the fluid line.

Optionally, after applying the vacuum and removing the residual air, the technician again applies pressure to the lubricant chamber but at a lower level than previously. That lower level of fluid pressure may remain in the lubricant chamber until the motor is being installed in a well.

Figure 1:
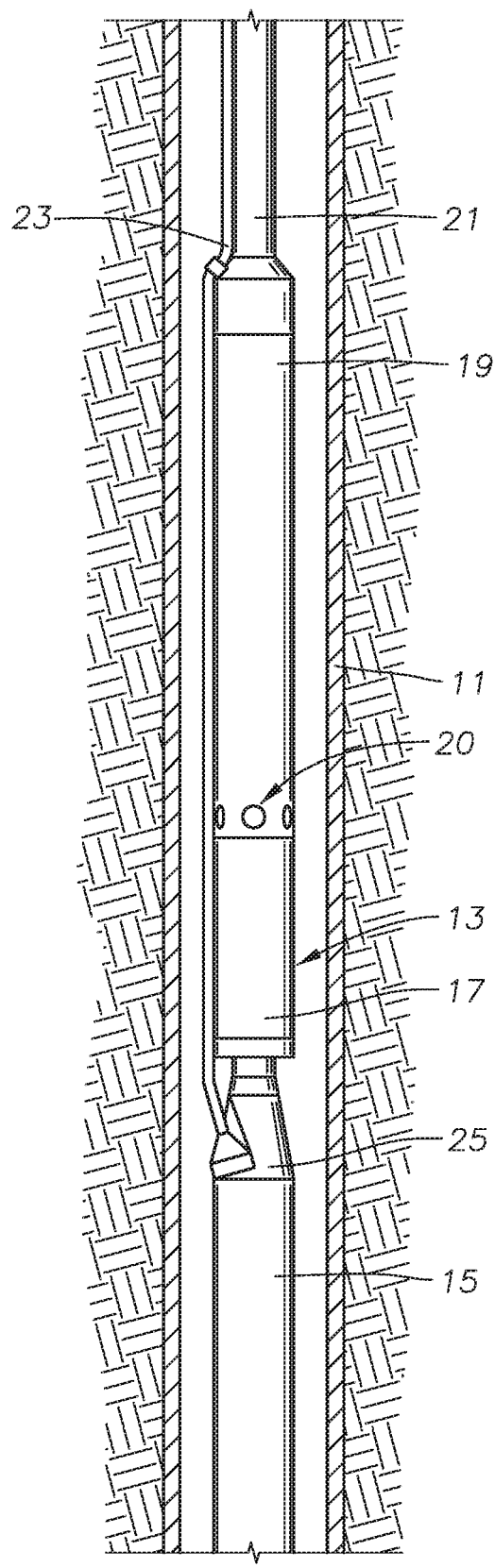
FIG. 1 is a schematic side view of an electrical submersible pump assembly having a motor with lubricant that has been checked for residual air and removed if found.

While the disclosure will be described in connection with the preferred embodiments, it will be understood that it is not intended to limit the disclosure to that embodiment. On the contrary, it is intended to cover all alternatives, modifications, and equivalents, as may be included within the scope of the claims.

DETAILED DESCRIPTION

The method and system of the present disclosure will now be described more fully hereinafter with reference to the accompanying drawings in which embodiments are shown. The method and system of the present disclosure may be in many different forms and should not be construed as limited to the illustrated embodiments set forth herein; rather, these embodiments are provided so that this disclosure will be thorough and complete, and will fully convey its scope to those skilled in the art. Like numbers refer to like elements throughout. In an embodiment, usage of the term "about" includes +/−5% of the cited magnitude. In an embodiment, usage of the term "substantially" includes +/−5% of the cited magnitude.

It is to be further understood that the scope of the present disclosure is not limited to the exact details of construction, operation, exact materials, or embodiments shown and described, as modifications and equivalents will be apparent to one skilled in the art. In the drawings and specification, there have been disclosed illustrative embodiments and, although specific terms are employed, they are used in a generic and descriptive sense only and not for the purpose of limitation.

FIG. 1 illustrates a cased well 11 having an electrical submersible well pump (ESP) 13 of a type commonly used to lift hydrocarbon production fluids from wells. The terms "upward", "downward", "above", "below" and the like are used only for convenience as ESP 13 may be operated in other orientations, such as horizontal.

ESP 13 has several modules that are secured together before installing them in well 11. These modules include an electrical motor 15 coupled by a seal section 17 to a centrifugal pump 19. Pump 19 has an intake port 20 that may be at the lower end of pump 19, in a separate module, or in an upper part of seal section 17 as shown. If a gas separator (not shown) is employed, intake port 20 would be in the gas separator.

Motor 15 contains a dielectric motor lubricant for lubricating the bearings within. Another module containing motor lubricant is a pressure equalizer, which communicates with the lubricant in motor 15 and with the well fluid. The pressure equalizer has a movable element, such as an elastomeric bag or a metal bellows, for reducing a pressure differential between the lubricant in motor 15 and the exterior well fluid. In this example, the pressure equalizer is a part of seal section 17. Alternately, the pressure equalizer could be located below motor 15, and other portions of seal section 17 could be above motor 15.

A string of production tubing 21 extending downward from a wellhead (not shown) supports ESP 13. Pump 19 discharges well fluid into production tubing 21. Alternately, ESP 13 could be secured to a string of coiled tubing located within a production conduit. In that event, pump 19 would discharge into an annulus surrounding the coiled tubing within the production conduit.

In this example, a power cable 23 extends downward alongside production tubing 21 and has a motor lead on its lower portion that connects to motor 15. If ESP 13 is installed on coiled tubing, power cable 23 would be inside the coiled tubing and motor 15 would normally be above pump 19.

Figure 2:
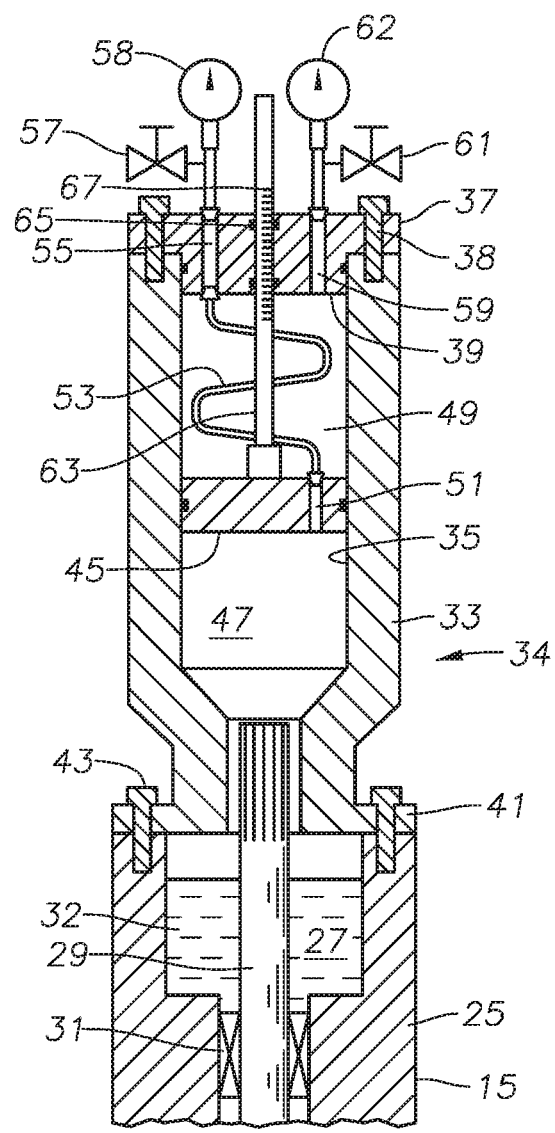
FIG. 2 is a schematic sectional view of an apparatus that is connected to the motor of FIG. 1 before the ESP is installed for determining if residual air is present in the lubricant.

Referring to FIG. 2, motor 15 may be conventional, having a head 25 attached to an upper end of a housing. Head 25 has a shaft passage 27 extending along a longitudinal axis. A drive shaft 29 extends through shaft passage 27 and rotates when motor 15 is powered. Radial support bearings 31 (one shown) provide radial support for shaft 29. A thrust bearing (not shown) will be at the upper end of shaft passage 27.

A dielectric lubricant 32 fills shaft passage 27 and other spaces in the interior of motor 15. The filling may be performed conventionally either at a factory, a field shop or a wellsite. A vacuum pump may be employed to first evacuate air from the interior of motor 15. Then lubricant 32 will be pumped in through a port in the lower end of motor 15.

FIG. 2 illustrates a test fixture 34 for determining if residual air is trapped in lubricant 32 in the interior of motor 15 after filling. Test fixture 34 includes a tubular body 33 that has a bore 35. A cap 37 with a seal member 39 at the upper end of body 33 closes and seals the upper end of bore 35. Seal member 39 may be attached to cap 37. Cap 37 secures to body 33 with threaded fasteners 38. Body 33 has an external flange 41 on its lower that secures to the upper end of head 25 with bolts 43.

A movable piston 45 seals in bore 35. Piston 45 divides bore 35 into a lubricant chamber 47 on its lower side and in this example, a pressure chamber 49 on its upper side. The volume of each chamber 47, 49 changes as piston 45 moves up and down. For example, the volume of lubricant chamber 47 decreases and the volume of pressure chamber 49 increases when piston 45 moves down.

Lubricant 32 may be introduced into lubricant chamber 47 in various manners. For example, if body 33 is attached to motor head 25 before motor 15 is filled, lubricant 27 being pumped in a lower end of motor 15 could also flow upward into bore 35. Motor 15 could be shipped pre-filled to a well site with body 33 and cap 37 in place. Piston 45 could be installed subsequently at the well site, if desired. Alternately, body 33 could have a fill port (not shown) to top up lubricant 32 in lubricant chamber 47 after body 33 is installed on a previously filled motor 15. Piston 45 may be in an uppermost position near cap 37 before testing begins.

In this embodiment, piston 45 has a port 51 that extends from its upper or pressure side to its lower or lubricant side. A flexible hose or fluid line 53 has an inlet that secures to the upper end of port 51. Fluid line 53 extends upward through pressure chamber 49 to a fluid line hole 55 that extends through seal member 39 and cap 37. A vacuum valve 57 attaches to cap 37 at the upper end or outlet of fluid line hole 55. A vacuum gauge 58 may be connected with vacuum valve 57 for monitoring pressure in fluid line 53 and lubricant chamber 47. Fluid line 53 has a length long enough to reach piston 45 while piston 45 is in a lowermost position at the lower end of lubricant chamber 47. When piston 45 is in its uppermost position near cap seal member 38, space in pressure exists for fluid line 53 to flex and axially contract.

A pressure chamber port 59 extends from the upper side of cap 37 to the lower side of seal member 39. A pressure valve 61 secures to cap 37 at the upper end of pressure port 59. A pressure gauge 62 may be mounted to pressure valve 61 to monitor the fluid pressure in pressure chamber 49. Pressure valve 61 has one position to admit pressurized fluid, such as air, into pressure chamber 49 and another position to vent the pressurized fluid into the atmosphere.

An indicator rod 63 secures to the upper side of piston 45 and extends upward through pressure chamber 49. Indicator rod 63 protrudes through a hole in seal member 39 and cap 37. Seals 65 seal indicator rod 63 within the hole through which it extends. Indicator rod 63 may be cylindrical and has visible indicia 67 formed on it to indicate an axial location of piston 45 in bore 35. Fluid line 53 may be coiled around indicator rod 63.

Figure 3:
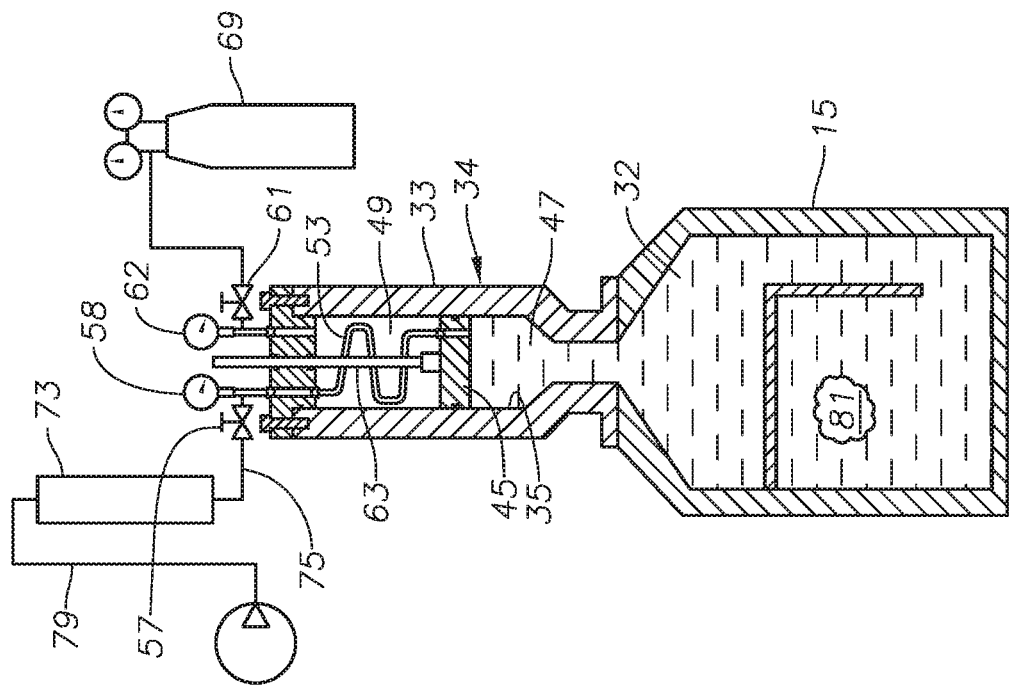
FIG. 3 is schematic section view of the apparatus of FIG. 2 connected with ancillary equipment as a first step for determining if trapped air is present.

Referring to FIG. 3, ancillary equipment to fixture 34 includes a fluid pressure source 69, such as a tank of compressed air or an air compressor. Pressure source 69 connects to pressure valve 61 with a pressure hose or line 71. The ancillary equipment also includes an air bubble monitoring device, which in this example is a sight glass 73. Sight glass 73 is a clear tube or container of glass, acrylic or the like. Sight glass 73 has closed upper and lower ends. A sight glass hose or line 75 extends from vacuum valve 57 to the lower end of sight glass 73. A vacuum pump 77 connects to the upper end of sight glass 73 via a vacuum hose or line 79.

After connecting fixture 34 to motor head 25 and connecting the ancillary equipment described, a technician will run a test to determine whether significant trapped air 81 exists in lubricant 32 within motor 15. Lubricant 32 will have been introduced into body bore 35 to a substantially full level. The level of lubricant 32 may place piston 45 in or near an uppermost position, as shown in FIG. 3. The technician will observe the axial location of piston 45 by noting indicia 67 at the upper side of cap 37. Motor 21 may be in a vertical position or other orientations. Any openings to motor 21, such as a receptacle for power cable 23 (FIG. 1), will be closed.

Figure 4:
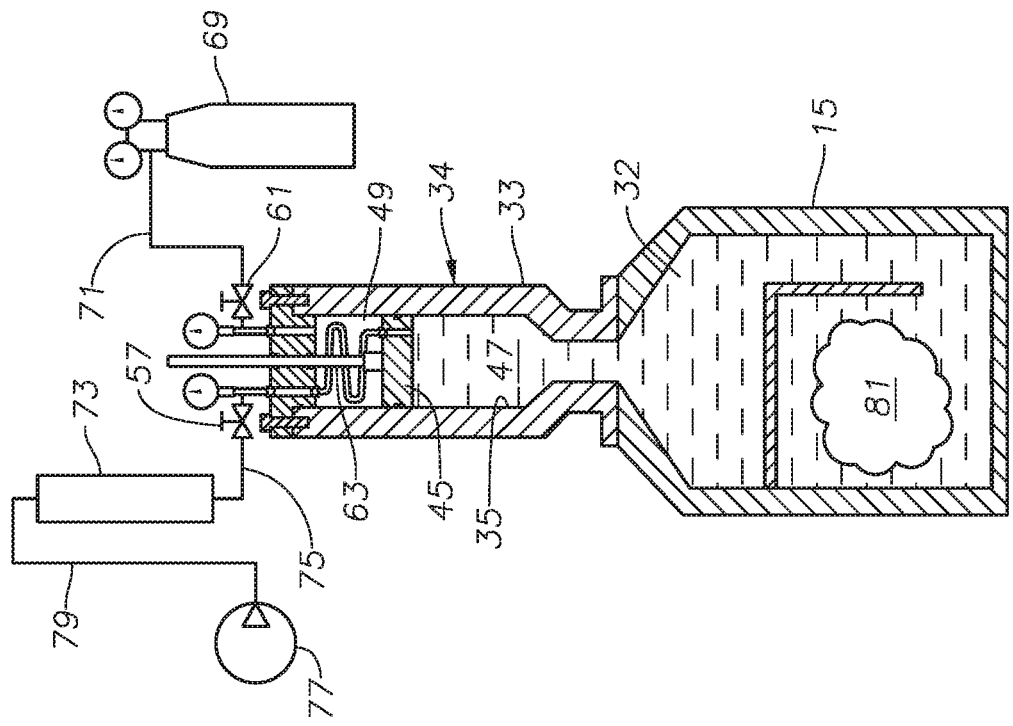
FIG. 4 is a schematic sectional view similar to FIG. 3, but illustrating a second step of applying pressure to the lubricant in the motor and monitoring downward movement of the indicator rod.

Referring to FIG. 4, the technician then applies a selected level of fluid pressure, which could be several hundred pounds per square inch, to pressure chamber 49 by opening pressure valve 61 to pressure source 69. Vacuum valve 57 will remain in a closed position. The fluid pressure acts on piston 45, increasing the fluid pressure of lubricant 32 in lubricant chamber 47 and in the interior of motor 15. Both pressure gauge 62 and vacuum gauge 58 will display the increased pressure.

Lubricant 32 is substantially incompressible at that pressure level. However, trapped air 81, if any, would be compressed by the fluid pressure, as schematically indicated in FIGS. 3 and 4. Because of the pressure, the volume of trapped air 81 decreases, resulting in downward movement of piston 45. The technician will note the distance that piston 45 moved downward by viewing indicia 67. Through previous empirical testing, the technician will determine whether that travel distance indicates an unacceptable volume of trapped air 81 in lubricant 32. Alternately, rather than applying pressure to pressure chamber 49, the pressure in lubricant chamber 47 could be increased by applying a controlled downward force on piston 45 through a mechanical device, such as a spring, screw, weights and the like.

Figure 5:
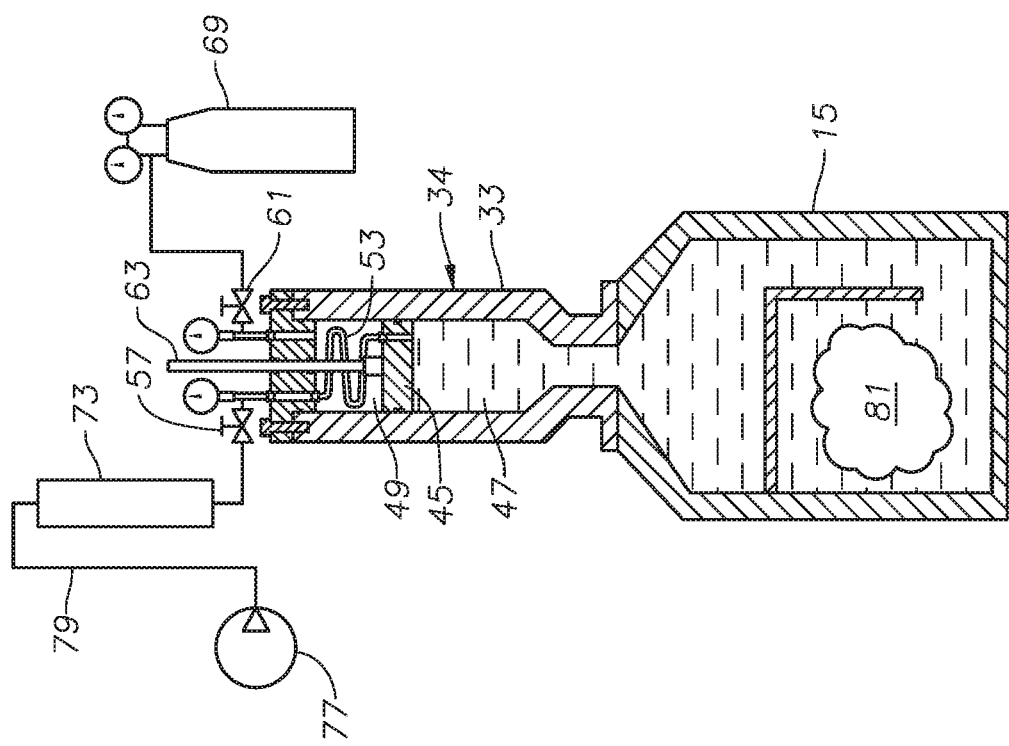
FIG. 5 is a schematic sectional view similar to FIG. 4, but illustrating a third step of opening a valve to an oil fill sight glass, which is the next step if too much residual air was found.

If the downward movement of piston 45 indicates an unacceptable amount of trapped air 81, a next step may be to remove trapped air 81. As indicated in FIG. 5, prior to attempting to remove trapped air 81, the technician relieves the fluid pressure in pressure chamber 49 by changing pressure valve 61 to a position that vents the pressurized air within pressure chamber 49 to atmosphere. The pressure in lubricant chamber 47 and the interior of motor 15 will return to atmospheric.

Then, as indicated in FIG. 5, the technician will apply a vacuum to lubricant chamber 47 and lubricant 32 in motor 15. He does this by opening vacuum valve 57 and turning on vacuum pump 77, which applies a vacuum to vacuum line 79, sight glass line 75 and fluid line 53. The pressure in pressure chamber 49 may remain at atmospheric. Sight glass 73 may be in a vertical position elevated above fixture body 33 and motor 15. The vacuum creates a suction that pulls lubricant 32 up through fluid line 53 to sight glass 73. The suction also causes trapped air 81 to disperse into smaller bubbles and migrate upward through fluid line 53 and sight glass line 75.

Figure 6:
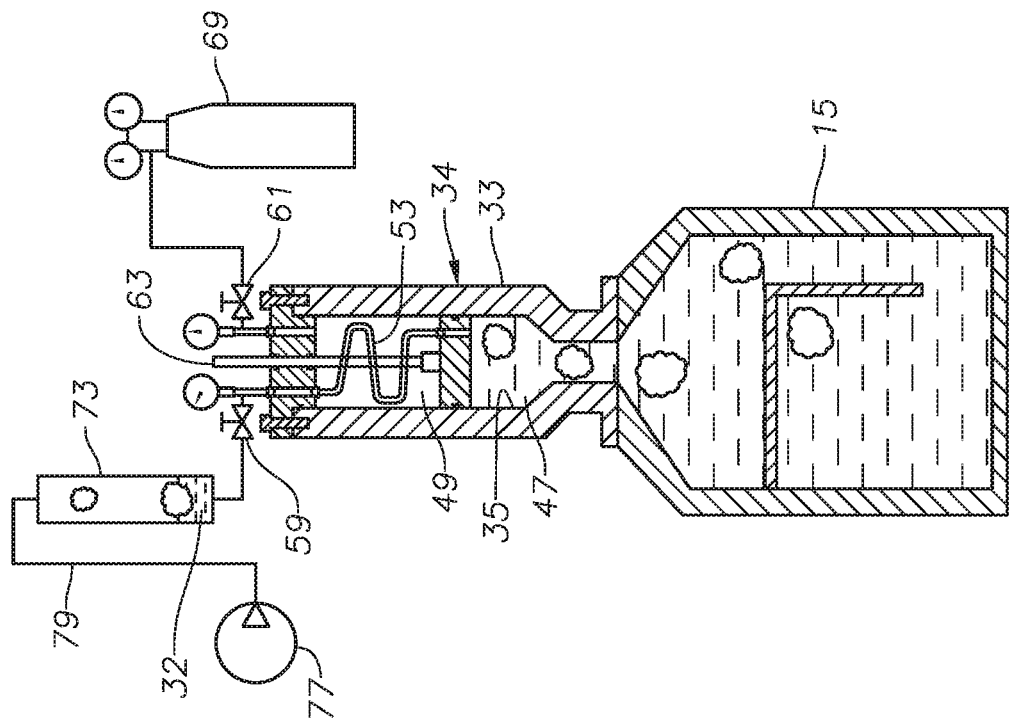
FIG. 6 is a schematic sectional view similar to FIG. 5, but illustrating a fourth step of operating the vacuum pump venting residual air through the oil fill sight glass.

By adjusting vacuum valve 57 to control the level of vacuum, the technician will control the upward flow of lubricant 32 through fluid line 53 and sight glass line 75 so as to place a static upper level of lubricant 32 within sight glass 73. The technician will observe this level, indicated in FIG. 6, which may be approximately between the lower and upper ends of sight glass 75. The technician can also observe in the lubricant level in sight glass 73 upward moving air bubbles from trapped air 81 in motor 15. Once in this static position, the level of vacuum may remain constant. The air bubbles migrating into sight glass 73 are drawn into vacuum line 79 and discharged into the atmosphere by vacuum pump 77. As trapped air 81 is removed, piston 45 will move downward in bore 35 because of the elimination of trapped air 81.

After air bubbles in sight glass 73 appear to have ceased, the technician shuts off vacuum pump 77 and closes vacuum valve 57 Lubricant chamber 47 will return to atmospheric pressure. The technician may then repeat the procedure described above to determine if trapped air 81 is still present by applying fluid pressure to pressure chamber 49 again and measuring the distance, if any, that piston 45 moves downward. If there is still a level of trapped air 81 above a selected amount, the operator repeats the step described above to remove trapped air 81.

The testing and residual air removal process described can be employed as part of conventional vacuum filling procedures. If the testing and trapped air removal procedure is performed at a well site, technicians will then remove fixture 34 from motor head 25. It may not be necessary to add any additional lubricant 32 to motor 15. Motor 15 will be assembled with seal section 17 and pump 19, then deployed in a well.

If the testing and trapped air removal procedure occurs at a factory or field shop, fixture 34 may remain attached to motor 21 until motor 21 is to be deployed in a well. Optionally, a small positive pressure may be applied to pressure chamber 49 by repeating the process illustrated in FIG. 3. The pressure level may be at a lower level than when testing to determine the existence of residual air. The small positive pressure retards the ingress of air into the interior of motor 15 and can be monitored from time to time.

Alternately, after testing and residual air elimination, piston 45 and valves 57, 61 may be removed from fixture body 33 while it remains attached to motor head 25. Leaving fixture body 33 attached provides room for thermal expansion of lubricant 32 during storage and shipping of motor 15. Although, lubricant 32 would not be at a positive pressure level above atmospheric, allowing thermal expansion of lubricant 32 can improve the lives of the various seals in motor 15.

Seal section 17 is another module that may be tested in a similar manner. Fixture 34 could be connected with the lubricant containing portion of seal section 17 and the same method applied to detect and remove trapped air in the lubricant containing portion of seal section 17. Also, motor 15 could be coupled to seal section 17 before testing and removing trapped air from the lubricant containing portion of seal section 17. In that instance fixture 34 would be connected to seal section 17, and the detection and removal of trapped air would occur in both motor 15 and seal section 17 at the same time.

The present disclosure described herein, therefore, is well adapted to carry out the objects and attain the ends and advantages mentioned, as well as others inherent therein. While one embodiment of the disclosure has been given for purposes of disclosure, numerous changes exist in the details of procedures for accomplishing the desired results. These and other similar modifications will readily suggest themselves to those skilled in the art, and are intended to be encompassed within the scope of the appended claims.

The invention claimed is:

1. An apparatus for determining the presence of and removing residual air from an electrical submersible well pump module prior to installing the module in a well, comprising;
 a tubular body that is adapted to be connected to the module;
 a bore in the body;
 a piston in the bore, the piston having a pressure side and a lubricant side, the piston defining on the lubricant side a lubricant chamber in the bore that is in fluid communication with the lubricant in the module after the body is connected to the module, the bore having a closed end that defines with the pressure side of the piston a pressure chamber in the bore;
 a pressure valve connected with the pressure chamber that enables fluid pressure to be applied to the pressure chamber;
 indicator means for determining a distance of travel of the piston, if any, in response to the fluid pressure being applied to the pressure chamber;
 a vacuum valve that is operable to apply a vacuum to the lubricant chamber to bleed out residual air from the lubricant in the module;
 a sight glass;
 a sight glass line extending from the vacuum valve to one end of the sight glass;
 a vacuum line extending from the vacuum pump to an opposite end of the sight glass;
 a vacuum pump that when operating applies a vacuum to vacuum line, the sight glass line, and the sight glass to draw lubricant from the lubricant chamber through the sight glass line into the sight glass, and the vacuum valve is selectively adjusted to define a barrier to lubricant flowing through the vacuum line to the vacuum pump and at the same time allowing air bubbles visible in the lubricant in the sight glass to flow through the vacuum line to the vacuum pump.

2. The apparatus according to claim 1, wherein the indicator means comprises:
 an indicator rod extending from the pressure side of the piston out a hole in the closed end of the bore; and
 indicia on the indicator rod for monitoring the distance of movement of the piston.

3. The apparatus according to claim 2, further comprising:
 a seal between the indicator rod and the hole in the closed end of the bore.

4. The apparatus according to claim 1, further comprising:
 a port extending through the piston from the pressure side to the lubricant side;
 a fluid line connected to the port and extending to the vacuum valve.

5. The apparatus according to claim 4, further comprising:
 a bubble monitoring device connected to the fluid line to detect residual air bubbles in the lubricant in the fluid line while the vacuum is being applied to the lubricant chamber.

6. The apparatus according to claim 1, further comprising:
 a flange with bolt holes on one end of the body for bolting the body to the module.

7. The apparatus according to claim 4, wherein the fluid line comprises a flexible hose extending through the pressure chamber.

8. The apparatus according to claim 1, wherein:
 the pressure valve has a position that vents the fluid pressure from the pressure chamber.

* * * * *